US012778693B2

(12) United States Patent
Amat Girbau

(10) Patent No.: US 12,778,693 B2
(45) Date of Patent: Nov. 3, 2026

(54) SENSORY PERCEPTION SURGICAL SYSTEM FOR ROBOT-ASSISTED LAPAROSCOPIC SURGERY

(71) Applicant: Rob Surgical Systems, SL, El Prat de Llobregat (ES)

(72) Inventor: Josep Amat Girbau, Barcelona (ES)

(73) Assignee: Rob Surgical Systems, SL, El Prat de Llobregat (ES)

(*) Notice: Subject to any disclaimer, the term of this patent is extended or adjusted under 35 U.S.C. 154(b) by 916 days.

(21) Appl. No.: 17/996,644

(22) PCT Filed: Apr. 16, 2021

(86) PCT No.: PCT/EP2021/059857
§ 371 (c)(1),
(2) Date: Oct. 20, 2022

(87) PCT Pub. No.: WO2021/219396
PCT Pub. Date: Nov. 4, 2021

(65) Prior Publication Data

US 2023/0218358 A1 Jul. 13, 2023

(30) Foreign Application Priority Data

Apr. 27, 2020 (EP) .................................... 20382338

(51) Int. Cl.
*A61B 34/35* (2016.01)
*A61B 17/29* (2006.01)
(Continued)

(52) U.S. Cl.
CPC .............. *A61B 34/35* (2016.02); *A61B 17/29* (2013.01); *A61B 34/71* (2016.02);
(Continued)

(58) Field of Classification Search
CPC .......... A61B 17/29; A61B 2018/00875; A61B 2018/1253; A61B 2018/126;
(Continued)

(56) References Cited

U.S. PATENT DOCUMENTS

| | | |
|---|---|---|
| 5,558,671 A | 9/1996 | Yates |
| 6,203,541 B1 | 3/2001 | Keppel |

(Continued)

FOREIGN PATENT DOCUMENTS

| | | |
|---|---|---|
| AU | 2017413263 A1 | 12/2019 |
| CL | 2019003223 A1 | 2/2020 |

(Continued)

OTHER PUBLICATIONS

European Patent Office; International Search Report and Written Opinion for PCT/EP2021/059857; Jul. 7, 2021; entire document.

*Primary Examiner* — Bradford C. Blaise
(74) *Attorney, Agent, or Firm* — ALLEN, DYER, DOPPELT + GILCHRIST, P.A.

(57) ABSTRACT

The present invention proposes a sensory perception system for robot-assisted laparoscopic surgery. The invention comprises an electrosurgical forceps coupled to a surgical tool, an electrocautery radiofrequency signal generator and an impedance measurement circuit. The latter includes a measurement sensor for measuring a signal indicative of a magnitude corresponding to the value of contact impedance between the forceps and a patient's tissue; an oscillator; a first electrical circuit with resistors and a voltage limiter for protecting the measurement sensor and the oscillator; and a second electronic circuit with switches. The sensor and the oscillator are connected to the forceps by means of a power cable of the surgical tool. A processor connected to the measurement circuit receives said measured signal and converts same into a force vector, the modulus of which is
(Continued)

a function of the contact impedance being measured and the argument is a function of the trajectory being followed.

10 Claims, 5 Drawing Sheets

(51) Int. Cl.
*A61B 18/00* (2006.01)
*A61B 18/12* (2006.01)
*A61B 34/00* (2016.01)

(52) U.S. Cl.
CPC ............... *A61B 2018/00875* (2013.01); *A61B 2018/1253* (2013.01); *A61B 2018/126* (2013.01)

(58) Field of Classification Search
CPC . A61B 18/1442; A61B 18/1445; A61B 34/30; A61B 34/35; A61B 34/71
See application file for complete search history.

(56) References Cited

U.S. PATENT DOCUMENTS

| | | | | |
|---|---|---|---|---|
| 6,840,938 | B1 | 1/2005 | Morely et al. | |
| 8,613,230 | B2 | 12/2013 | Blumenkranz et al. | |
| 10,575,900 | B2 | 3/2020 | Laughner et al. | |
| 10,595,745 | B2 | 3/2020 | Byron et al. | |
| 2003/0100892 | A1 | 5/2003 | Morley et al. | |
| 2008/0046122 | A1 | 2/2008 | Manzo et al. | |
| 2011/0046659 | A1 | 2/2011 | Ramstein et al. | |
| 2012/0041436 | A1 | 2/2012 | Ullrich et al. | |
| 2012/0209303 | A1 | 8/2012 | Frankhouser et al. | |
| 2013/0165869 | A1* | 6/2013 | Blumenkranz ...... | B25J 15/0009 606/130 |
| 2016/0045247 | A1* | 2/2016 | Heim ................. | A61B 18/1206 |
| 2016/0143686 | A1* | 5/2016 | Tunay ................ | A61B 18/1233 606/34 |
| 2017/0215802 | A1* | 8/2017 | Byron .................... | A61B 5/068 |
| 2020/0078113 | A1 | 3/2020 | Sawhney et al. | |
| 2021/0015574 | A1* | 1/2021 | Atay ...................... | A61B 34/74 |
| 2021/0068916 | A1* | 3/2021 | Hu ......................... | A61B 18/00 |
| 2021/0077180 | A1* | 3/2021 | Govari ................... | A61B 18/14 |

FOREIGN PATENT DOCUMENTS

| | | | |
|---|---|---|---|
| CN | 106535809 | A | 3/2017 |
| EP | 2595587 | | 12/2015 |
| JP | S5277490 | A | 6/1977 |
| JP | 2006288431 | A | 10/2006 |
| WO | WO2016153561 | | 9/2016 |

* cited by examiner

SENSORY PERCEPTION SURGICAL SYSTEM FOR ROBOT-ASSISTED LAPAROSCOPIC SURGERY

FIELD OF THE INVENTION

The present invention generally relates to the field of robot-assisted surgery. Particularly, the invention relates to a sensory perception surgical system for robot-assisted laparoscopic surgery which allows detecting the properties of a patient's tissue, particularly the contact force exerted on the tissue, through the measurement of electrical impedance.

BACKGROUND OF THE INVENTION

Current robot-assisted laparoscopic surgery techniques allow carrying out high-precision interventions, providing relevant advantages, particularly in surgeries of certain complexity, for example in surgeries where it is difficult to access the operation site. Nevertheless, current robot-assisted laparoscopy surgery techniques present the drawback of the surgeon not perceiving the forces exerted on the anatomical elements of the patient.

Robotic arms are used in a robot-assisted laparoscopic surgery for actuating specific tools which allow performing the intervention effectively, and for introducing and guiding a camera which allows viewing the operative field. These robotic arms are remotely controlled by a surgeon by means of a control panel provided with a screen that allows the surgeon to monitor the scene. Likewise, besides improving surgical precision, the use of computers associated with robotic arm control also allows introducing controls that provide greater safety to the patient.

In recent years, significant efforts have been made in the field of research to enable providing sensory return to the surgeon making up for the loss of tactile sensation when the intervention is a manual intervention.

Patent application US 2011046659-A1 describes a minimally invasive surgical tool including a sensor that generates a signal in response to an interaction with the surgical tool. The tool further includes a haptic feedback system that generates vibrations to obtain a haptic effect in response to the signal.

On the other hand, U.S. Pat. No. 8,613,230-B2 discloses a system which allows measuring forces from a sensor installed in the outer part of the cannula of the surgical tool, and receives the forces in the axis of penetration Z through a mechanical transmission sheath. The system described in this patent only allows perceiving said forces exerted on the axis of penetration Z, and not the forces derived from lateral contacts.

To enable perceiving forces exerted not only in the direction of the axis of penetration Z, elastic elements which allow measuring three-dimensional deformations by means of interferometry using optical sensors have been used, like in the case of patent EP2595587-B1. In this case, 3 or 4 optic fibers which allow projecting modulated light on a reflector located on an elastic support are used and the force vector applied on the forceps is obtained by means of interferometry from the outer part of the cannula.

Patent CA 2870343 presents an alternative to the use of elastic elements integrated on the cannula. To that end, a sensor with 6 degrees of freedom is used, which sensor allows supplying the forces and torques produced between the outer distal end of the tool and the end where the tool is held with the robotic arm which supports same. The system includes a computer system which allows calculating, by means of matrix calculus, the forces applied on the distal end based on the kinematics of the tool-trocar assembly and the 6 pieces of data supplied by the sensor.

WO2016153561 discloses a medical instrument that comprises an elongate body having a proximal end and a distal end and a pair of electrodes or electrode portions (for example, a split-tip electrode assembly). The system is configured to perform contact sensing and/or ablation confirmation based on electrical measurements obtained while energy of different frequencies are applied to the pair of electrodes or electrode portions. The contact sensing systems and methods may calibrate network parameter measurements to compensate for a hardware unit in a network parameter measurement circuit or to account for differences in cables, instrumentation or hardware used.

U.S. Pat. No. 10,595,745-B2 discloses devices and methods for measuring a contact force on a catheter. The catheter includes a proximal segment, a distal segment, and an elastic segment extending from the proximal segment to the distal segment. The distal segment includes a plurality of tip electrodes including at least three radial electrodes disposed about a circumference of the distal segment. The radial electrodes are configured to output electrical signals indicative of a contact vector of the contact force. The elastic segment includes a force sensing device configured to output an electrical signal indicative of a magnitude of an axial component of the contact force, wherein the contact force is determined by scaling the magnitude of the axial component of the contact force by the contact vector. In this document, the measurement of the contact force is done mechanically, not electrically as in present invention.

US2003100892-A1 discloses a robotic surgical tool that includes an elongate shaft having a working end and a shaft axis, and a pair of linking arms each having a proximal end and a distal end. The proximal end is pivotally mounted on the working end of the shaft to rotate around a first pitch axis to produce rotation in first pitch. A wrist member has a proximal portion pivotally connected to the distal end of the linking arm to rotate around a second pitch axis to produce rotation in second pitch. An end effector is pivotally mounted on a distal portion of the wrist member to rotate around a wrist axis of the wrist member to produce rotation in distal roll. The wrist axis extends between the proximal portion and the distal portion of the wrist member. The elongate shaft is rotatable around the shaft axis to produce rotation in proximal roll. At about 90° pitch, the wrist axis is generally perpendicular to the shaft axis. The proximal roll around the shaft axis and the distal roll around the wrist axis do not overlap. The use of the linking arms allows the end effector to be bent back beyond 90° pitch. The ability to operate the end effector at about 90° pitch and to bend back the end effector renders the wrist mechanism more versatile and adaptable to accessing hard to reach locations, particularly with small entry points such as those involving spinal, neural, or rectal surgical sites.

In another line of work known as Vison-Based Force Sensing (VBFS), the actual images captured by the laparoscopic camera are used to view the tissue deformation caused by contact with the forceps.

In any case, sensory return has practically not been used in robot-assisted laparoscopic surgery due to technique limitations, the imprecision of different developed systems, or the difficulties it entails, particularly the space occupied by the sensorization on the cannula of the tool.

New surgical systems for robot-assisted laparoscopic surgery, which allow detecting the properties of a tissue/tissues and quantifying the sensory return of the contact force exerted on the tissue/tissues during a surgical intervention performed remotely, are therefore required.

DESCRIPTION OF THE INVENTION

To that end, the embodiments of the present invention provide a sensory perception surgical system for robot-assisted laparoscopic surgery comprising: an electrosurgical forceps coupled to a surgical tool, an impedance measurement circuit and an electrocautery radiofrequency signal generator electrically coupled to the impedance measurement circuit and operable for supplying energy, as both monopolar and bipolar energy, to the electrosurgical forceps. The impedance measurement circuit includes a measurement sensor for measuring a signal indicative of a magnitude corresponding to the value of a contact impedance between the electrosurgical forceps and a patient's tissue; an oscillator for providing a power signal to the measurement sensor; a first electrical circuit and a second electronic circuit. The first electrical circuit includes one or more resistors and a voltage limiter for protecting the measurement sensor and the oscillator that are connected to the electrosurgical forceps by means of a power cable of the surgical tool. The second electronic circuit comprises a first switch circuit for commutating between the connection and the disconnection of a power cabling of the electrocautery radiofrequency signal generator with respect to the cable of the surgical tool, and a second switch circuit for commutating between the connection and the disconnection of the electrocautery radiofrequency signal generator and the measurement sensor.

Likewise, the proposed system includes at least one processor operatively connected to the electrocautery radiofrequency signal generator and to the impedance measurement circuit for receiving said signal measured by the measurement sensor and converting same into a force vector. Particularly, the modulus of the force vector is a function of the measured contact impedance and the argument is defined by the trajectory the surgical tool follows in the moment of contact.

Therefore, the mentioned processor allows obtaining the vectorial reaction force on the operator's controls, both in magnitude and in orientation, based on the measured magnitude of the contact impedance, which varies according to the force being exerted, and on the monitoring of the trajectory being followed.

In one embodiment, the proposed system also includes a radiofrequency detector with at least one capacitive or inductive sensor arranged on the mentioned power cabling for automatically commutating the first and second switch circuits while supplying energy.

In one embodiment, the energy supplied by the electrocautery radiofrequency signal generator is monopolar. In this case, the first switch circuit is formed by one relay and the second switch circuit is formed by another relay. Alternatively, when the supplied energy is bipolar, the first switch circuit is formed by at least two relays and the second switch circuit is also formed by at least two relays.

The system may further include a control unit comprising control elements operatively connected to the impedance measurement circuit and/or to the electrocautery radiofrequency signal generator for the control thereof. For example, the control elements may include pedals and/or actuators/push buttons.

The processor may be included in the control unit or in a remote computation device and operatively connected to the control unit, the electrocautery radiofrequency signal generator, and/or the impedance measurement circuit by means of a cable or wireless connection.

In one embodiment, the electrosurgical forceps are coupled to the surgical tool using a set of pulleys and cables which allow the opening or closing, as well as the mobility, of the forceps. At least one of the pulleys is arranged on the articulation shaft thereof. Likewise, the set of pulleys is arranged on three parallel shafts arranged in a diametrical position with respect to the surgical tool and to a body of the electrosurgical forceps.

Other embodiments of the invention disclosed herein also include a computer-implemented method and/or computer program products for performing the steps and operations performed by the mentioned processor. More particularly, a computer program product is an embodiment having a computer system-readable medium including code instructions coded therein which, when executed in at least one processor of the computer system, cause the processor to perform the operations indicated herein as embodiments of the invention.

In one embodiment, the anatomy of the surroundings of the tissue/tissues is modeled based on the force vector estimated by the processor. To that end, the surface is progressively modeled by means of defining polygonal surfaces, such as for example triangles that are being formed by joining adjacent contact points obtained during the operation/intervention.

Therefore, the present invention allows determining the force vector based on the measurement of a magnitude of the contact impedance between the forceps and the patient's tissues and on the trajectory taken, and it also allows constructing a three-dimensional model of the surgical environment.

One advantage provided by the present invention is that it does not introduce any additional sensor on the electrosurgical forceps, which allows being able to use the same conductors used for carrying out electrocauterization or electrocoagulation, for example.

BRIEF DESCRIPTION OF THE DRAWINGS

The foregoing and other features and advantages will be better understood based on the following detailed description of several merely illustrative and non-limiting embodiments in reference to the attached drawings in which:

FIG. 5A shows a perspective view of a distal end of the surgical tool showing rotations G1 and G2 of the articulations thereof and axial rotation G3 of the surgical tool assembly. FIG. 5B shows the pulleys for the transmission of movements G1 and G2 and the arrangement of the actuator cables which also allow the opening or closing of the electrosurgical forceps through rotation G1.

DETAILED DESCRIPTION OF THE INVENTION

The present invention provides a sensory perception surgical system for robot-assisted laparoscopic surgery and a method allowing obtaining the sensory return of the force exerted by a surgeon on a patient's tissue/tissues during a surgical intervention performed remotely based on an estimate of the force vector exerted by detecting the contact impedance with the tissue/tissues and on the trajectory taken.

Figure 1:
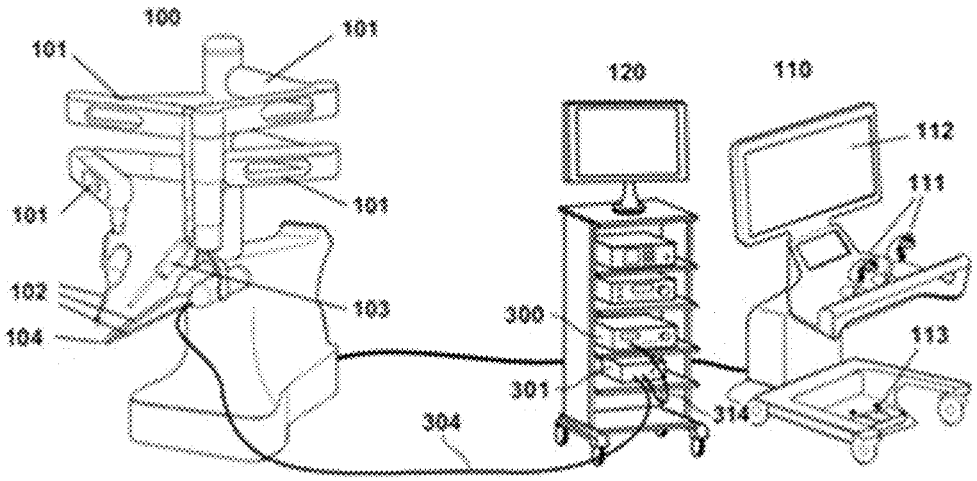
FIG. 1 illustrates a surgical system for robot-assisted laparoscopic surgery for detecting the properties of a tissue, according to an embodiment of the present invention.

With reference to FIG. 1, said figure shows an embodiment of the proposed system 1. In this embodiment, the system 1 comprises a robot-assisted system 100; a control unit 110; a laparoscopy tower 120 housing an electrocautery radiofrequency signal generator 300 and an impedance measurement circuit 301.

The robot-assisted system 100 is provided with robotic arms 101 which allow moving surgical tools 102, as well as a laparoscopic camera 103. The control unit 110 includes actuators/push buttons 111 and pedals 113 with which the surgeon can handle/control the robot-assisted system 100, the electrocautery radiofrequency signal generator 300, as well as the impedance measurement circuit 301. The control unit 110 also has a display screen 112.

The electrocautery radiofrequency signal generator 300, which can be any standard electrocauterization signal generator, is electrically connected to the impedance measurement circuit 301 by means of a power cable 314 and is operable for supplying energy to the electrosurgical forceps 104 (see FIGS. 2A-2C, for example) coupled to the surgical tools 102. The impedance measurement circuit 301 is electrically connected to the electrosurgical forceps 104 by means of another power cable 304. The power cable 304 is formed by two conductor cables 304*a*, 304*b* (see FIG. 6D), the path of which is compatible with the kinematics of the electrosurgical forceps 102, allowing the movements thereof in three rotations/axes (orientation and elevation movements, as well as opening and/or closing movements) to enable detecting contact with the tissue/tissues.

Figure 5A:
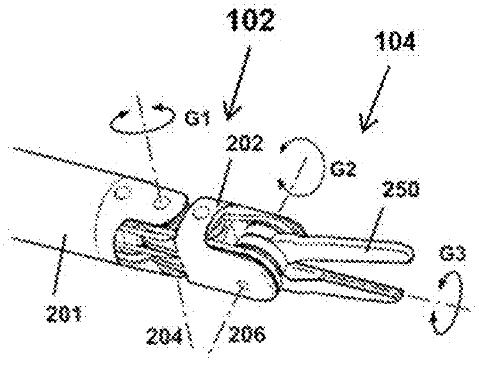
FIGS. 5A and 5B show different views of the electrosurgical forceps coupled to the surgical tool.

The electrocautery radiofrequency signal generator 300 can be electrically monopolar when the return circuit is the patient him/herself or the saline medium used (FIG. 2A), or it can be electrically bipolar (FIGS. 2B and 2C) if the current flows between the terminal element 250 (see FIGS. 5A-5B) of the electrosurgical forceps 104.

Figure 2A:
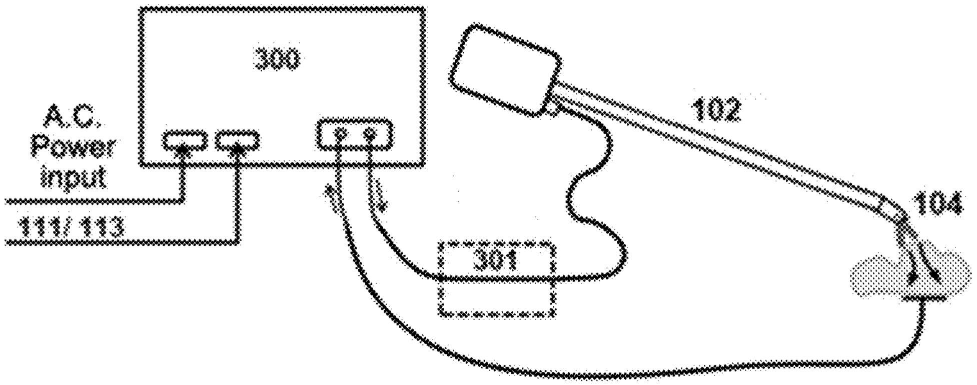
FIGS. 2A-2C schematically illustrate different connection configurations of an electrocautery radiofrequency signal generator for working in monopolar mode (FIG. 2A) or bipolar mode (FIGS. 2B and 2C).
Figure 2B:
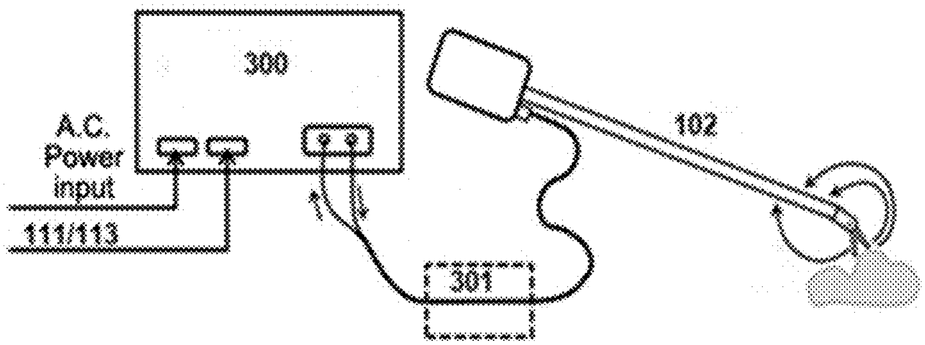
Figure 2C:
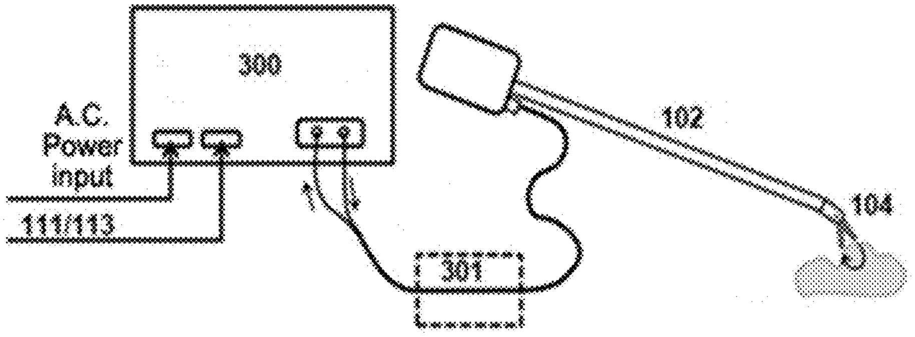

FIG. 2A shows a monopolar configuration. The impedance measurement circuit 301 only houses one cable, i.e., the outgoing power cable. The incoming cable, marked with the arrow, passes outside the impedance measurement circuit 301. FIG. 2B shows a first bipolar configuration. The double incoming and outgoing cable with two polarities, marked with arrows, exits the electrocautery radiofrequency signal generator 300 and passes through the impedance measurement circuit 301, wherein the return is taken back through a conducting cannula. FIG. 2C shows a second bipolar configuration. The cable with two conductor wires exiting the electrocautery radiofrequency signal generator 300 pass through the impedance measurement circuit 301 and travel along the inside thereof, one to each part of the electrosurgical forceps 104.

Figure 3:
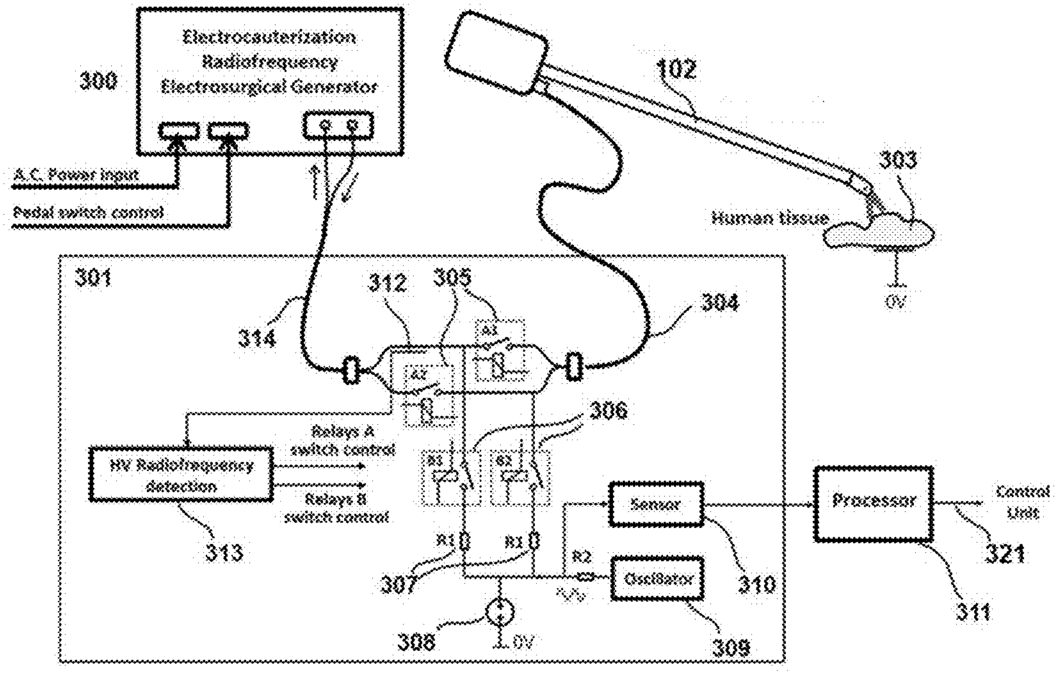
FIG. 3 illustrates in more detail the architecture of the system proposed for obtaining the contact impedance and the associated force vector, according to an embodiment of the present invention.

Now with reference to FIG. 3, said figure shows another embodiment of the proposed system 1, comprising in this case the electrosurgical forceps 104 coupled to the surgical tool 102 of the robot-assisted system 100; the impedance measurement circuit 301 for measuring the contact impedance with the environment 303 of the tissue/tissues; the electrocautery radiofrequency signal generator 300; and a computer system or device 311 formed by at least one processor for estimating the applied forces based on the measurement of the impedance.

The difficulty entailed by use of the electrocautery radiofrequency signal generator 300 to enable also measuring contact impedance lies in the fact that radiofrequency pulses having a very high voltage of between about 1000 and 3000 volts are used to enable carrying out electrocoagulation and electrocauterization. For this reason, the use or inclusion of the impedance measurement circuit 301 in the proposed system 1 makes the measurement of the impedance at a low voltage and current compatible with the high electrocoagulation and electrocauterization energy at a high voltage.

To achieve the mentioned compatibility, the impedance measurement circuit 301 includes a measurement sensor 310, particularly a low-voltage measurement sensor, for measuring the magnitude corresponding to the value of the contact impedance; an electronic module comprising two switch circuits 305, 306 for the connection/disconnection of the power cabling 314 with respect to the power cable 304, and for the connection/disconnection of the electrocautery radiofrequency signal generator 300 and the measurement sensor 310, respectively.

Likewise, the impedance measurement circuit 301 also includes an oscillator 209 to enable measuring the impedance without applying any current, however weak it may be, with a continuous component, on the patient. The oscillator 209 provides a signal having a low voltage, for example 6 V, and a medium frequency, for example 20 KHz, which is applied in a monopolar or bipolar manner to the surgical tool 102 through the second switch circuit 306, the contacts of which are usually kept closed. Said low voltage is normally not applied to the electrocautery radiofrequency signal generator 300 since the contact of the first switch circuit 305 is usually open.

In the embodiment of FIG. 3, each of the switch circuits 305, 306 comprises two relays A1, A2, B1, B2. This configuration is particularly useful when the energy supplied by the electrocautery radiofrequency signal generator 300 is bipolar. In other embodiments not illustrated in this case, and particularly when the energy supplied by the electrocautery radiofrequency signal generator 300 is monopolar, each of the switch circuits 305, 306 only includes one relay A1, B1.

In operation, when the surgeon applies the energy for carrying out electrocoagulation or electrocauterization, the contact of relay A1, or relays A1, A2 of the first switch circuit 305 must be closed, while at the same time the contact of relay B1, or relays B1, B2 of the second switch circuit 306 must be open. To that end, the system 1 also particularly includes a radiofrequency detector 313 having a capacitive or inductive sensor 312 on the power cable 314, which allows automatically commutating the first and second switch circuits 305, 306 while energy is being applied. Alternatively, this function may be performed by introducing the actuation signal of the pedals 113 connected to the electrocautery radiofrequency signal generator 300.

In the example of FIG. 3 and for the purpose of preventing damage in the electrocautery radiofrequency signal generator 300 and/or in the impedance measurement circuit 301, for example as a result of surges in the commutation of the relays, the system 1 is particularly protected with resistors 307 and a voltage limiter 308.

The signal/magnitude corresponding to the value of the impedance obtained by the measurement sensor 310 is treated by the processor 311 for conversion into a force vector, in which the force magnitude is given by the value of the impedance being measured and the argument of the vector is defined by the direction in space of the trajectory that the surgical tool 102 follows in the moment of contact and is controlled by the control unit 110 which is connected to the processor 311 through a communication channel 321.

Figure 4:
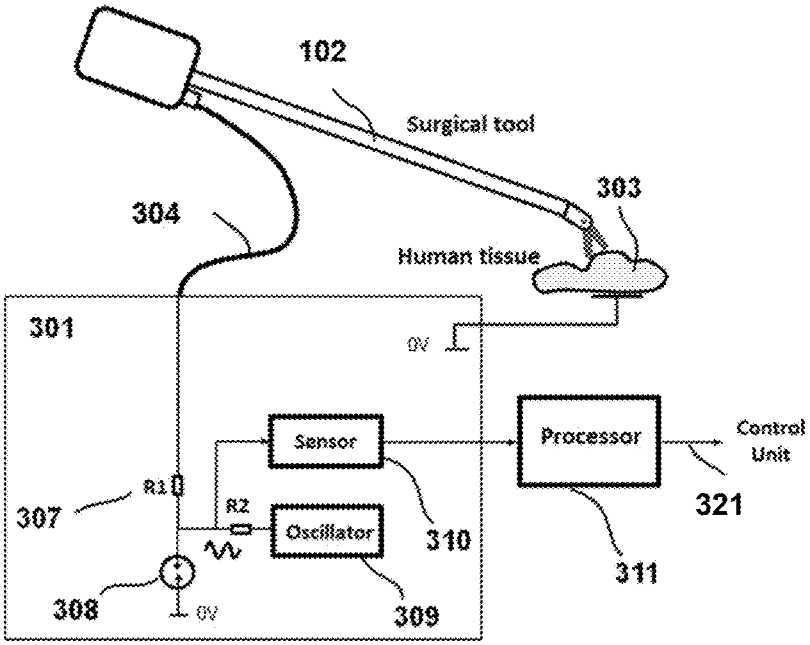
FIG. 4 illustrates another embodiment of the architecture of the system proposed for obtaining the contact impedance and the associated force vector.

FIG. 4 shows another embodiment of the proposed system 1. In this case, the system 1 is formed by the electrosurgical forceps 104 coupled to the surgical tool 102; the impedance measurement circuit 301 for measuring the contact impedance with the environment 303 of the tissue/tissues; and the computer system or device 311 comprising at least one processor. The impedance measurement circuit 301 includes the measurement sensor 310, the oscillator 309, and an electronic circuit formed by the resistors 307 and the voltage limiter 308. Compatibility with high external voltages like in the case of using the electrocautery radiofrequency signal generator 300 is therefore permitted.

Each surgical tool 102 (see FIGS. 5A and 5B) is made up of a cannula 201 supporting a first articulated element or body 202 which can carry out rotation G1 with respect to the end of the cannula 201 about shaft 204 actuated by a drum 207. The body 202 supports the terminal element 250 of the electrosurgical forceps 104 the orientation of which can be varied by carrying out rotation G2 with respect to the body 202 about shaft 206 actuated by means of drums 208 and 209.

Figure 5B:
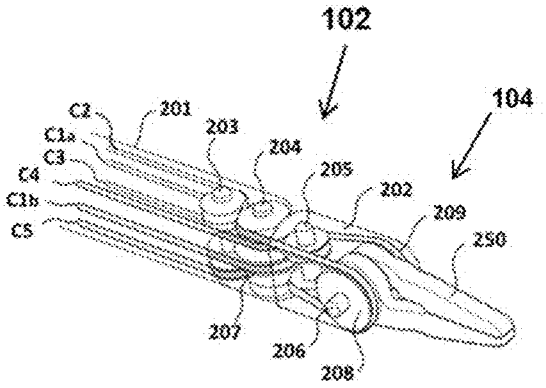

Likewise, cables C1*a*, C1*b*, C2, C3, C4, and C5 and a set of pulleys 210, 211, 212, 213, 220, 221, 222, 223, 230, 231 allow transmitting the movement from drive means to which each surgical tool 102 is connected, and are adapted to enable carrying out rotation G1 about shaft 204, which entails a mechanical complexity that hinders the introduction of the electrical cables 304*a* and 304*b*. This mechanical complexity is of great relevance since the electrical conductors for measuring the impedance must share the smaller space available with the two cables C1*a* and C1*b* which transmit rotational movement G1 to the drum 207, and the four cables C2, C3, C4, and C5 which transmit the orientation and opening or closing of the electrosurgical forceps 104 by means of drums 208 and 209 (FIG. 5B).

Figure 6A:
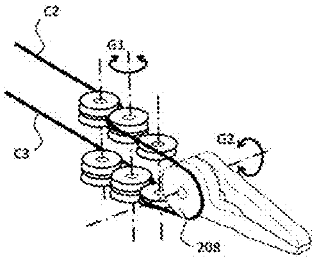
FIGS. 6A-6D illustrate different views showing the path of the cables which transmit energy to the electrosurgical forceps for detecting contact with the tissue, where said path must be compatible with the limited space available between the different pulleys, and also allows carrying out rotations G1, G2, and G3.
Figure 6B:
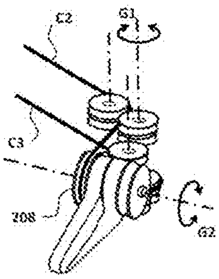
Figure 6C:
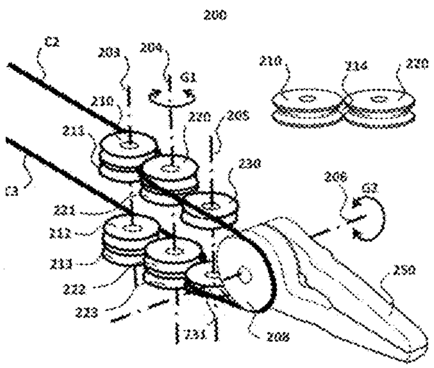

To allow rotation G1 the mentioned set of pulleys 210, 211, 212, 213, 220, 221, 222, 223, 230, 231 is used, in which at least one, preferably all, of said pulleys is/are arranged on the articulation shaft thereof (FIG. 6A). Particularly, as observed in FIG. 6B, a set of pulleys is arranged for the four cables C2, C3, C4, and C5 which move the electrosurgical forceps 104, mounted on three parallel shafts 203, 204, and 205 in a diametrical position with respect to the cannula 201 and to the body 202 (FIG. 5B). The central shaft 204 joins the cannula 201 and the body 202, which allows carrying out rotation G1, and supports the 4 pulleys 220, 221, 222, and 223 joining the two pairs of antagonist cables transmitting the movement of the forceps, whereas the two shafts 203 and 205 support accompanying pulleys.

This arrangement of pulleys on three consecutive shafts for each cable that must go through articulation G1 offers a clear advantage over other embodiments, given that besides allowing the generation of a guided cable passage between consecutive pulleys, like in the case of pulleys 210 and 220 which create passage 214 (see FIG. 5C), constituting a secure guiding of the movement of each cable, two free spaces are created on pulleys 230 and 231 allowing the passage of the necessary electrical cable 304*a* and 304*b* to enable measuring the impedance.

Figure 6D:
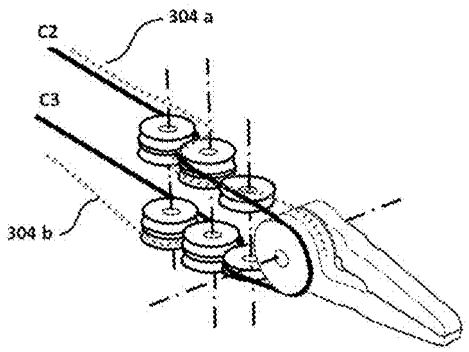

The fact that all the pulleys are arranged on the central plane of the cannula 201 and of the body 202 allows the pulleys to have the largest possible diameter without exceeding the maximum gauge of the cannula 201. Likewise, with the 4+4+2 pulleys required for the transmission of movements having the largest possible diameter, the present invention allows reducing the radius of curvature of the different cables on the pulleys, improving the durability and reliability of the surgical tool 102. The electrical cable 304*a* and 304*b* going through the free spaces on the pulleys 230 is integral with cables C2 and C3, assuring that that it does not support any mechanical force when deflexion of the electrosurgical forceps 104 on axis G2 occurs (FIG. 6D).

The embodiments of the present invention also provide a sensory perception method for estimating or calculating the reaction force vector that must be perceived by the surgeon or the operator in the control unit 110, through the push buttons/actuators 111 and/or pedals 113, based on the value/magnitude of the obtained impedance.

Figure 7A:
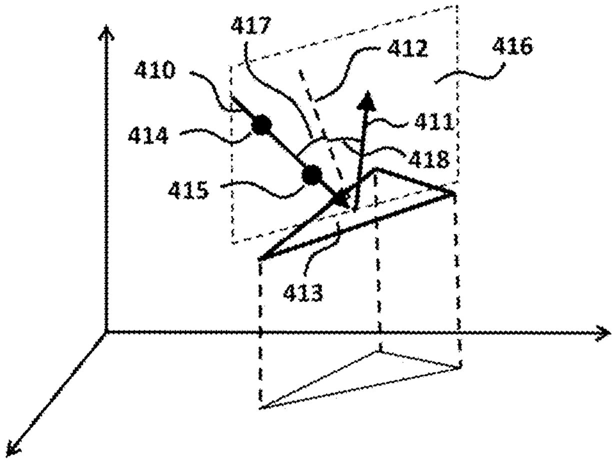
FIGS. 7A-7C graphically depict the calculated force vector and the construction of the triangles for modeling the anatomy of the environment, according to an embodiment of the present invention.
Figure 7B:
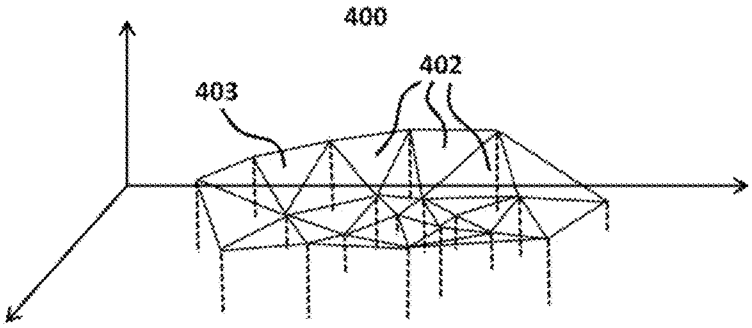
Figure 7C:
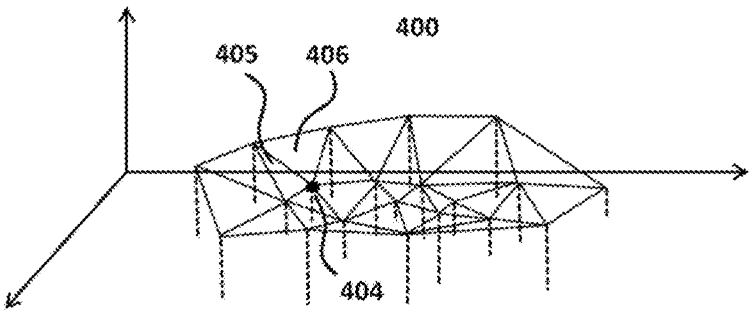

FIGS. 7A-7C graphically illustrate an example of the foregoing. Given that there is no force sensor on the surgical tool 102 which allows the direct measurement of the contact force 410 (FIG. 7A), it is estimated indirectly by the processor 311 as a force vector. The force vector 411 is estimated as a reflected vector of the contact force 410, the modulus of which is equal to the modulus of the contact force 410, whereas the argument thereof is defined by being on the same plane 416, and which is defined by the two passage points 414 and 415 before the perceived contact point, the normal 412 of the contact surface 413, and an angle of reflection 418 that is equal to the angle incidence 417.

The contact surface 413 which allows carrying out positioning calculations in space of the reflected vector is not known. Therefore, the proposed method obtains an approximation of the configuration of the surface of the anatomical elements of the environment by performing modeling 400 in a three-dimensional space. To that end, the method comprises generating a triangulation 402 (i.e., generating a series of triangles 403) from the contact points 404 that are perceived throughout the operation, by means of joining same. Each new perceived contact point 404 (FIG. 9C) causes a triangle 403 to be broken down into new triangles 405 and 406. In this manner, the environment modeling resolution which allows obtaining the argument of the force vector 411, which is applied as a reaction force on the controls of the control unit 110 and generates the sensory return to the surgeon/operator, progressively increases.

The proposed invention can be implemented in hardware, software, firmware, or any combination thereof. If it is implemented in software, the functions can be stored in or coded as one or more instructions or code in a computer-readable medium.

The scope of the present invention is defined in the attached claims.

What is claimed is:

1. A sensory perception surgical system for robot-assisted laparoscopic surgery comprising:

an electrosurgical forceps coupled to a surgical tool;

an electrocautery radiofrequency signal generator electrically coupled to an impedance measurement circuit and configured to supply energy to the electrosurgical forceps;

the impedance measurement circuit comprising:

a measurement sensor configured to measure a signal indicative of a magnitude corresponding to a value of a contact impedance between the electrosurgical forceps and a patient's tissue;

an oscillator configured to provide a power signal to the measurement sensor;

a first electrical circuit comprising one or more resistors and a voltage limiter configured to protect the measurement sensor and the oscillator, the measurement sensor and the oscillator being connected to the electrosurgical forceps by a power cable of the surgical tool; and a second electronic circuit comprising a first switch circuit configured to commutate between a connection and a disconnection of a power cabling of the electrocautery radiofrequency signal generator with respect to the power cable of the surgical tool, and a second switch circuit configured to commutate between a connection and a disconnection of the electrocautery radiofrequency signal generator and the measurement sensor; and a radiofrequency detector comprising at least one capacitive or inductive sensor disposed on the power cabling and configured to automatically commutate the first switch circuit and the second switch circuit while supplying energy, and a processor operatively connected to the impedance measurement circuit and configured to receive the signal measured by the measurement sensor, the processor further configured to convert the signal into a force vector, the force vector being estimated as a reflected vector of the received signal, a modulus of the force vector being a function of the contact impedance and an argument of the force vector being defined by a trajectory followed by the surgical tool in the moment of contact.

2. The system according to claim 1, wherein the electrocautery radiofrequency signal generator is configured to supply the energy as both monopolar and bipolar energy.

3. The system according to claim 1, wherein the supplied energy is monopolar, the first switch circuit and the second switch circuit each includes a relay.

4. The system according to claim 1, wherein the supplied energy is bipolar, the first switch circuit and the second switch circuit each comprise at least two relays.

5. The system according to claim 1, further comprising a control unit comprising control elements operatively connected to the impedance measurement circuit and the electrocautery radiofrequency signal generator, the control elements cooperatively configured to control each of the impedance measurement circuit and the electrocautery radiofrequency signal generator.

6. The system according to claim 5, wherein the control elements comprise pedals and/or actuators/push buttons.

7. The system according to claim 5, wherein the processor is disposed in the control unit.

8. The system according to claim 1, wherein the electrosurgical forceps are coupled to the surgical tool using a set of pulleys and cables cooperatively configured to allow opening or closing of the electrosurgical forceps and enable mobility thereof.

9. The system according to claim 8, wherein the set of pulleys are disposed on three parallel shafts, each one of the three parallel shafts arranged in a diametrical position with respect to the surgical tool and to a body of the electrosurgical forceps.

10. A non-transitory computer readable medium comprising program code instructions that when executed by a processing unit are configured to implement a method for estimating a reaction force vector perceived in a control unit of a sensory perception surgical system that includes the processing unit, an electrosurgical forceps coupled to a surgical tool, an impedance measurement circuit and an electrocautery radiofrequency signal generator electrically coupled to the impedance measurement circuit and operable for supplying energy to the electrosurgical forceps, the impedance measurement circuit including a measurement sensor, an oscillator, a first electrical circuit comprising one or more resistors and a voltage limiter, and a second electronic circuit comprising a first switch circuit and a second switch circuit, the method comprising:

receiving a signal indicative of a magnitude corresponding to a value of a contact impedance between the electrosurgical forceps and a patient's tissue, measured by the measurement sensor; and converting the received signal into a force vector estimated as a reflected vector of the received signal, a modulus of the force vector being a function of the contact impedance and an argument of the force vector being defined by a trajectory followed by the surgical tool in the moment of contact.

* * * * *